United States Patent [19]

Hughes et al.

[11] Patent Number: 4,997,763

[45] Date of Patent: Mar. 5, 1991

[54] VECTORS FOR GENE INSERTION INTO AVIAN GERM LINE

[75] Inventors: Stephen H. Hughes, Smithburg, Md.; Donald W. Salter, Haslett; Lyman B. Crittenden, Williamston, both of Mich.

[73] Assignee: The United States of America as represented by the Secretary of Agriculture, Washington, D.C.

[21] Appl. No.: 80,278

[22] Filed: Jul. 31, 1987

[51] Int. Cl.$^5$ .............................................. C12N 15/00
[52] U.S. Cl. ........................... 435/172.3; 800/DIG. 1; 800/2; 435/317.1; 935/32
[58] Field of Search ................... 435/172.3, 320, 317.1; 935/32; 80C/2, DIG. 1

[56] References Cited

PUBLICATIONS

H. L. Robinson et al., "Sequences Outside of the Long Terminal Repeat Determine the Lymphomogenic Potential of Rous-Associated Virus Type 1," J. Virol. 55(3): 752–759, (Sep. 1985).
Harriet L. Robinson et al., "At Least Two Regions of the Viral Genome Determine the Oncogenic Potential of Avian Leukosis Viruses," Proc. Natl. Acad. Sci. U.S.A. 79: 1225–1229, (Feb. 1982).
S. H. Hughes et al., "Genes for the Major Structural Proteins: Organization and Control of Expression," In Cold Spring Harbor annual report, pp. 81–86, (1981).
S. H. Hughes, "Sequence of the Long Terminal Repeat and Adjacent Segments of the Endogenous Avian Virus Rous-Associated Virus O," J. Virol. 43(1): 191–200, (Jul. 1982).
S. H. Hughes et al., "Genes for the Major Structural Proteins: Organization and Control of Expression," In Cold Spring Harbor annual report, pp. 85–92, (1982).
S. Hughes et al., "Retroviral Vectors," In Cold Spring Harbor annual report, pp. 66–68, (1983).
S. H. Hughes et al., "Gene Expression in Eucaryotes," In Litton Bionetics, Inc. Basic Research Program annual report, pp. VI-73 to VI-81, (1984).
S. Hughes et al., "Mutagenesis of the Region between env and src of the SR-A Strain of Rous Sarcoma Virus for the Purpose of Constructing Helper-Independent Vectors," Virology 136: 89–99, (1984).
S. H. Hughes et al., "Gene Expression in Eukaryotes Section," In Litton Bionetics, Inc. Basic Research Program annual report, pp. 138–147, (1985).
L. B. Crittenden et al., "Gene Insertion: Current Progress and Long-Term Goals," Avian Dis. 30(1): 43–46, (Jul. 23, 1985).
L. B. Crittenden et al., "Genetic Engineering to Improve Resistance to Viral Diseases of Poultry: A Model for Application to Livestock Improvement," Can. J. Anim. Sci. 65: 553–562, (Sep. 1985).
R. M. Shuman et al., "Gene Transfer by Avian Retroviruses," Poul. Sci. 65: 1437–1444, (Aug. 1986).
D. W. Salter et al., "Retroviruses as Vectors for Germ Line Insertion in the Chicken," Proc. Symp. on Molecular Approaches to Poultry Breeding and Disease Resistance, Third World Congress on Genetics Applied to Livestock Production, (in print Jul. 1986).
S. H. Hughes et al., "Design of Retroviral Vectors for the Insertion of Foreign Deoxyribonucleic Acid Sequences into the Avian Germ Line," Poul. Sci. 65: 1459–1467, (Aug. 1986).
D. W. Salter et al., "Gene Insertion into the Chicken Germ Line by Retroviruses," Poul. Sci. 65: 1445–1458, (Aug. 1986).

Primary Examiner—Elizabeth C. Weimar
Assistant Examiner—Jasemine C. Chambers
Attorney, Agent, or Firm—M. Howard Silverstein; Curtis P. Ribando; John D. Fado

[57] ABSTRACT

A stable, substantially nononcogenic vector having a cloning site for the convenient insertion of a gene of interest has been constructed by recombinant technology from an avian retrovirus. The construct is derived from Rous sarcoma virus and the cloning site is a replacement for the src oncogene. This vector is useful for ferrying selected, expressible genes into avian germ cells for incorporation into the germ line. The vector is also useful for inserting and expressing foreign genes in somatic avian cells both in vivo and in vitro.

4 Claims, 3 Drawing Sheets

VECTORS FOR GENE INSERTION INTO AVIAN GERM LINE

BACKGROUND OF THE INVENTION

1. Field of the Invention

Increasing genetic variability as a base for increased progress in animal breeding has been a long-term goal of agricultural research. Advances in molecular genetics suggest to us that it will soon be possible to introduce specific desirable genes into domestic animals.

The raw material for animal improvement is genetic variation. Recent advances in molecular genetics open the possibility for transferring new genetic information to the germ line of various species. Desirable genes could then be introduced into an improved line of domestic animals and these strains used for further improvement. For example, in chickens, egg production strains are highly susceptible to avian leukosis virus (ALV), and efforts to reduce the rate of congenital infection are underway by commercial breeders. Introduction of a dominant gene for resistance to ALV infection in available egg production strains would achieve this goal and thereby demonstrate that economically important new genes can indeed be introduced into the genome of a food animal species without disrupting the breeding program.

2. Description of the Prior Art

Insertion of foreign deoxyribonucleic acid (DNA) into the germ line of the mouse by microinjection of DNA into the male pronucleus of the newly fertilized ovum is now routine [Brinster et al., Proc. Natl. Acad Sci. USA 82: 4438–4442 (1985); Wagner, Can. J. Anim. Sci. 65: 539–552 (1985)]. Using similar techniques, genetic modification of economically important farm animals, such as pigs and sheep, has recently been reported [Hammer et al., Nature 315: 680–683 (1985)]. Because of the difficulty of manipulating new fertilized ova reviewed in Wagner, supra; Crittenden et al., Can. J. Anim. Sci. 65: 553–562 (1985); Freeman et al., World Poult. Sci. J. 41: 124–132 (1985); and Hughes et al., Poult. Sci. 65: 1459–1467 (1986)]similar results in the fowl have not been reported. However, natural insertion of genetic information into the chicken germ line has been occurring since the speciation of the chicken [Frisby et al., Cell 17: 623–634 (1979); Astrin et al., Cold Spring Harbor Symposium 44: 1105–1109 (1980); and Hughes et al., Cold Spring Harbor Symposium 44: 1077–1091 (1980)]. At least 22 endogenous viral genomes (proviruses) have been identified and characterized in the White Leghorn. Many more exist in other commercial lines of chickens [Hughes et al., Virology 108: 222–229 (1981); Gudkov et al., J. Gen. Virol. 57: 85–94 (1981)]. The presence of these proviruses suggests that there is a natural mechanism for proviral integration into the germ line. Presumably, retroviral infection of germ cells occurs on rare occasions. Spontaneous germ line insertion of murine leukemia virus has been detected in some strains of mice [Rowe et al., Proc. Natl. Acad. Sci. USA 77: 4871–4874 (1980); Herr et al., Nature 296: 865–868 (1982); Jenkins et al., Hybrid Mic. Cell 43: 811–819 (1985)]. That this can be done experimentally was shown first by Jaenisch, Proc. Natl. Acad. Sci. USA 73: 1260–1264 (1976) using retroviral infection of early mouse embryos and more recently by Van Der Putten et al., Proc. Natl. Acad. Sci. USA 82: 6148–6152 (1985) by infection of early mouse embryos with a retroviral vector.

Retroviruses offer substantial advantages for use as vectors both in cultured cells and in the intact animal [for a comprehensive review of the properties of retroviruses, see Weiss et al., RNA Tumor Viruses (1982)]. Retroviruses are the only viruses that behave as vectors in higher eukaryotes in nature. As such, it was reasonable to expect that these viruses could be readily adapted as vectors capable of accepting a wide variety of DNA sequences after suitable manipulations in the laboratory; a prediction that has been shown to be correct over the last few years. In addition, retroviruses can insert a DNA copy of their genomes into germ cells of a variety of species of higher eukaryotes in nature. Therefore, it is reasonable to expect to make use of these viruses, after inserting the desired sequences, as vectors for insertion of foreign DNA into the germ line. This has been done successfully both in the murine and in the avian systems. As vectors, these viruses offer other advantages as well.

Retroviral genomes are small, making it relatively easy to manipulate a cloned DNA copy of the genome. The viruses are efficient; in culture, essentially all of the cells can be infected. Most retroviruses are nonlytic; infection has little or no effect on cells in culture, and retroviruses exist that have no obvious deleterious effects on the intact animal. Since a DNA copy of the viral genome integrates into the host genome, the progeny of a single infected cell are all infected, and the provirus is in the same place in the genome of each of the progeny cells. Infection is self-limiting; each infected cell usually acquires 1–5 copies of the viral genome. Intervening sequences can be removed from genomic inserts cloned into a retroviral vector upon passage of the recombinant virus in cultured cells [Sorge et al., J. Mol. Appl. Genet. 1: 547–559 (1982); Shimotohno et al., Nature 299: 265–268 (1982)].

Unfortunately, there are also some disadvantages. Retroviruses, and the vectors derived from them, are relatively unstable. When a helper virus is present, there is extensive recombination, and even in the absence of a helper, internal rearrangements are frequently seen. The total size of the vector, including both the viral and nonviral sequences, is limited to about 10–11 kb [Shimotohno et al., Cell 26: 67–78 (1981); Sorge et al., J. Mol. Appl. Genet. 1: 547–559 (1982), supra; and Sorge et al., In Eukaryotic Viral Vectors, Y. Gluzman, ed., Cold Spring Harbor Laboratory, Cold Spring Harbor, N.Y., pp. 127–133 (1982); Joyner et al., Mol. Cell. Biol. 3: 2180–2190 (1983); Norton et al., Mol. Cell. Biol. 5: 281–290 (1985)].

In our consideration for use of retroviral vectors intended for the insertion of genetic information into the germ line of chickens, it became apparent that the design of the vectors would be influenced by several important criteria. The ideal vector would be highly infectious, at least for the germ cells, so that a significant proportion of the progeny will have acquired the new genetic information. However, the vector should, upon entering the germ line, be incapable of further rounds of infection, so that it would become a stable part of the germ line, and so that in subsequent generations no reinfection of either germ line or somatic tissue would occur. The viral vector itself should have little or no adverse effect on the physiology of the host, and should not cause disease either in the host or in any other species. Finally, the vector should insert itself into many locations in the host genome. This may be important because the position may affect expression of the inserted information, and will be essential if a bird carrying two of more markers inserted by the same vector is to be created.

SUMMARY OF THE INVENTION

We have now for the first time constructed a retroviral vector which has the essential properties for inserting selected genes into the avian genome. We have also devised an effective method for using the vector to introduce specific genes into an avian germ line for expression in a Mendelian fashion.

The vector is a construct derived from Rous sarcoma virus which is highly oncogenic in poultry. Elimination of oncogenicity in the vector is accomplished by removing the oncogene, src, and by replacing a region having an enhancer that can activate host oncogenes with a weak enhancer from a related and comparatively nononcogenic endogenous avian virus. New genetic information can be inserted in place of the deleted src gene and expressed as proteins. The vector is stabilized against deletion of the gene of interest by elimination of one of the direct repeat sequences in the noncoding region of the original virus. Segments superfluous to replication and gene expression are also eliminated.

In accordance with this discovery, it is an object of the invention to construct a substantially nononcogenic vector for inserting desired and heritable genes into the avian genome.

Another object of the invention is to derive stable, helper-independent, and defective retroviral vectors from Rous sarcoma virus and the endogenous viruses of the chicken.

A further object of the invention is to construct vectors capable of inserting and expressing foreign genes in somatic avian cells both in vivo and in vitro.

It is also an object of the invention to produce transgenic poultry by introducing an expressible foreign gene into the germ line.

Other objects and advantages of this invention will become readily apparent from the ensuing description.

GLOSSARY

For purposes of this invention, the following abbreviations, terms, and gene nomenclature used herein have been defined below. Also listed are the cleavage sites of the restriction enzymes referred to in the specification.

ABBREVIATIONS

ALV = avian leukosis virus (exogenous oncogenic virus)
bp = basepair
DR = direct repeat
ev = endogenous virus - used in conjunction with a number to identify loci in chicken genome
G0 = generation of host infected with an exogenous virus
G1 = first generation progeny of G0
G2 = second generation progeny of G0
kb kilobases (1000 base pairs)
LTR = long terminal repeat
PBS = primer binding site
PPT = polypurine tract
RAV = Rous-associated virus
RAV-0 = Rous-associated virus, Type 0 (endogenous, nononcogenic chicken virus)
RSV = Rous sarcoma virus (exogenous, oncogenic chicken virus)
SA = splice acceptor
SD = splice donor
SR-A = Schmidt-Ruppin A (strain of RSV)

TERMS clone: in reference to DNA, the product or process of isolating a segment of DNA, linking it to a replicon, and introducing it into a host for expansion coding region: a region of genetic information (RNA or DNA) that encodes a particular protein or polypeptide endogenous: refers to DNA provirus which is principally passed vertically (in the genome) from one host generation to another exogenous: refers to retrovirus which infects its host by horizontal passage from one animal to another, or nongenically to progeny expression: the transcription of a gene into messenger RNA (mRNA) and the subsequent translation of the mRNA into a protein coded by the gene foreign gene: a gene not normally present in a particular genome, cell, or vector gene of interest: a gene, usually a foreign gene, which is desired to be inserted into genome, cell, or vector infection: the introduction of bacteria or virus into cells or into a living organism wherein the bacteria or virus can replicate linker: synthetic oligonucleotide usually containing a site for a restriction enzyme noncoding region: a region of genetic information (RNA or DNA) that does not protein or polypeptide permuted: refers to a base sequence or region in which the order of the genes has been altered relative to the order found in nature polylinker: array of recognition sites (each of which is usually 4-8 bases long) linked together subclone: in reference to DNA, the product or process of cloning a portion of an already cloned DNA segment transfection: introduction of new genetic material into a cell transgenic: relating to new genetic information becoming embedded into a germline vector: a derivative of a virus or plasmid constructed by recombinant DNA techniques and having a cloning site or sites for inserting new DNA or RNA sequences pBR322: a standard plasmid cloning vector
pPH: a derivative of pBR322 which lacks the ClaI restriction enzyme site
λgt WES: a standard cloning vector derived from the E. coli virus λ

GENE NOMENCLATURE env: retroviral gene which encodes the envelope antigens that determine the antigenic and subgroup specificity of the progeny virus
gag: retroviral gene which encodes group-specific or internal antigens
pol: retroviral gene which encodes reverse transcriptase and the endonuclease
src: the oncogene carried by the Rous sarcoma virus
c-src: endogenous form of src, a normal cellular gene
v-src: viral form of src

| Restriction Enzyme | Cleavage Site |
| --- | --- |
| AccI | GT↓$^{AG}_{CT}$AC |
| BalI | TGG↓CCA |
| ClaI | AT↓CGAT |
| EcoRI | G↓AATTC |
| HindIII | A↓AGCTT |
| PvuII | CAG↓CTG |
| SstI | GAGCT↓C |
| TaqI | T↓CGA |

DETAILED DESCRIPTION OF THE INVENTION

Construction of the Vector. For purposes of this invention, we have chosen to begin with helper-independent retroviral vectors. Helper-independent vectors offer certain advantages. There is no requirement for a helper (cell or virus), and, in general, this gives a significant increase in stability. Also, there is no requirement for the vector to carry a selectable marker. As long as the helper-independent construction is itself stable, any sequence inserted into the vector will be passively carried to all infected cells as a part of the viral genome. Inserts that can be introduced into these vectors range in size up to about 2 kb in length.

Rous sarcoma virus (RSV) derives from an avian leukosis virus (ALV) and is the only known helper-independent retrovirus that carries a host-derived oncogene. This gene, called src, is an acquired cellular oncogene and can be removed and replaced by other genes. Hereafter, the term "c-src" will be used to distinguish the src coding region in the chicken genome from the analogous region, v-src, in the retrovirus. We have chosen to construct the vectors from the SR-A (Schmidt-Ruppin A) strain of RSV. The procedure for inserting foreign genes in place of src has been previously described in Hughes and Kosik, Virol. 136: 89–99 (1984); Sorge and Hughes, J. Virol. 43: 482–488 (1982); Sorge and Hughes, J. Mol. Appl. Genet. 1: 547–559 (1982), supra; Sorge and Hughes, In "Eucaryotic Viral Vectors" (Y. Gluzman, ed.), pp. 127–132, Cold Spring Harbor Laboratory, Cold Spring Harbor, NY, supra; Sorge, Ricci, and Hughes, J. Virol. 48: 667–675 (1983), all herein incorporated by reference.

The basic strategy of the insertion procedure is a multistep process in which the v-src coding region is excised, an insertion site is provided in the excision region, and the gene of interest is thereafter inserted into the insertion site. In some of the vectors the inserted gene is stabilized by also excising one of the direct repeat segments either in conjunction with the v-src excision or in a separate step. In addition, the oncogenicity is diminished by replacing the long terminal repeat (LTR) region with the LTR of a substantially nononcogenic virus. In practice, the large circular form of DNA from the SR-A strain of RSV is cloned as a permuted linear into the phage, λgt WES. Subsequent manipulations are then performed on fragments of the linear which are subcloned into pBR322 or related plasmids. One such plasmid is pPH, which is a derivative of pBR322 lacking the ClaI site. These plasmids can be grown in E. coli and selected by a drug-resistant trait or other selection criteria as known in the art.

The v-src coding region can be deleted as a part of any of a variety of different segments. The strategy for making the deletion is to: (1) remove as many nonessential sequences as possible; (2) create matched joints so as to minimize, and preferably eliminate, any overlap in the region flanking the insertion site; and (3) to retain or provide the sequences necessary to facilitate transcription of the inserted gene to be able to maximize its expression. We have found by experimentation that there is a considerable degree of latitude which can be exercised in terms of the size of the segment deleted, provided that the above criteria are met.

Figure 1A:
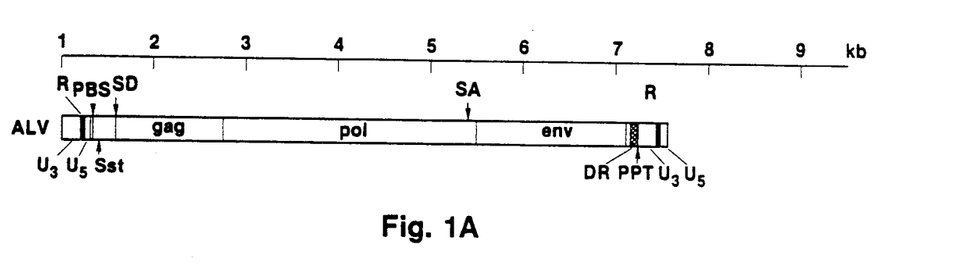
FIG. 1A is a molecular map of an avian leukosis virus (ALV).

FIG. 1A schematically illustrates, as a standard for comparison, the linear structure of an ALV virus. At the top of the drawing is a scale in kilobases. Represented in the drawing are the principal sequences of interest. The three genes required for viral replication, gag, pol, and env, are indicated. These are called the "coding sequences" or "coding regions" required for viral replication. Gag encodes the group-specific or internal antigen. Pol encodes reverse transcriptase which copies the RNA into a linear provirus DN and also the endonuclease required for insertion of the DNA genome of the virus into the genome of the host. Env encodes the envelope antigens that determine the antigenic and subgroup specificity of the progeny virus. The complete virus particle is formed at the cell membrane and buds from it. There are several distinct envelope antigens of the exogenous ALV's that are called subgroups A through D.

The endogenous proviruses are inherited as single gene loci which are sometimes transcribed and expressed. All endogenous env genes characterized so far in chicken encode subgroup E envelope antigen that is readily distinguished from the exogenous env products. In addition to the coding sequences, retrovirus contain several important noncoding regions. The two ends of the viral genome include the regions labelled $U_3$, R, and $U_5$ which are copied by reverse transcriptase to form direct repeats found at the ends of the proviral DNA. These long terminal repeats (LTRs) are important for efficient integration into the host genome and serve as promoters for the transcription of the viral genome and messenger (m)RNA. During the viral life cycle, a viral DNA molecule is inserted into the host chromosome at a large number of sites. Host enzymes transcribe the DNA to viral genomic RNA and mRNA that is translated to form viral proteins. To the right of the left hand LTR is the primer binding site (PBS) which binds a host tRNA to permit the proper initiation of viral DNA synthesis. Also illustrated are an SstI restriction enzyme site just downstream from the PBS, a splice donor (SD), a splice acceptor (SA), a direct repeat sequence, and the polypurine tract (PPT), all of which will be described in further detail below.

Figure 1B:
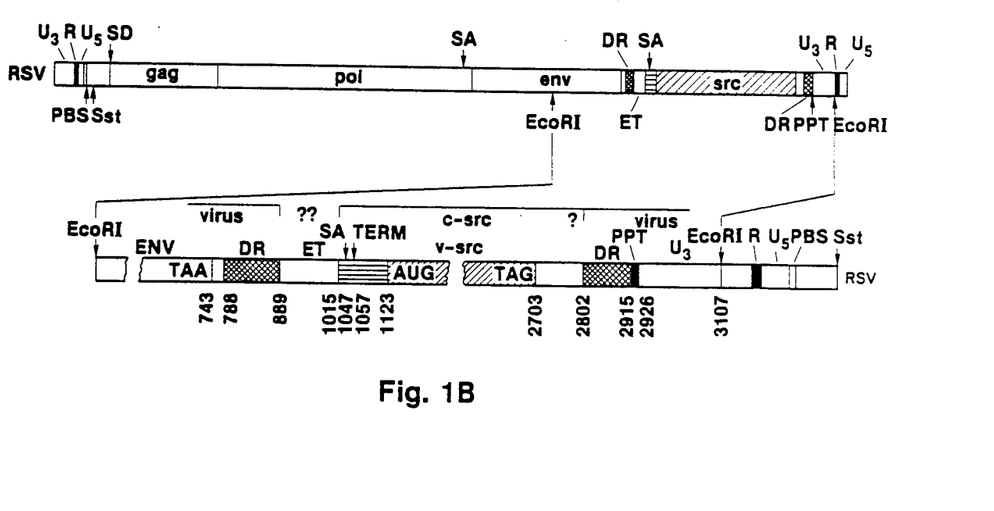
FIG. 1B is a molecular map of Rous sarcoma virus (RSV) with the region downstream from the EcoRI site in the env gene shown on an expanded scale.

FIG. 1B schematically illustrates the structure of the SRA strain of RSV. Regions analogous to the ALV virus are similarly labeled. In addition, RSV contains the v-src oncogene which is best seen on the expanded scale and is flanked by a pair of direct repeats. To the right of the upstream DR is a region of unknown origin called "E.T." To the right of E.T. is a region including a second splice acceptor. The site labeled "TERM" is a translational termination required for proper translation of src. Also shown are an EcoRI site in the downstream $U_3$ region and a second SstI site. The numbers below the expanded scale denote the distance from the EcoRI site in env. Hereafter, the term "upstream" will refer to base sequences or nucleic acid segments to the left of a given reference point, and the term "downstream" will refer to sequences or segments to the right. By convention, linear representations of RNA and the upper strand of double stranded DNA progress from the 5' end on the left to the 3' end on the right. Accordingly, the upstream sequences are sometimes referred to in the literature as "5'," and the downstream sequences as "3'."

The v-src coding region is removed from a subclone of SR-A DNA in a two-part process: first, the DNA is cleaved with a suitable combination of endonucleases and exonucleases to create the desired upstream and downstream fragments flanking the deletion; and second, the upstream fragment is ligated, or linked, to the downstream fragment to yield the vector. To facilitate the joining together of the fragments, a linker containing a common restriction site is attached to each of the respective fragments, and the respective subclones are then digested with the appropriate restriction enzyme. The restriction site which remains as an artifact of this joining can then be used as the insertion site for the desired foreign gene.

For generating the endpoint on the upstream fragment, it is preferable to start with a 3.1 kilobase (kb) subclone which consists of a segment including the last 719 base pairs of the env gene and includes the first 177 base pairs of the LTR. By digesting the subclone with either AccI or BalI restriction enzyme, the segment will be cut at either 882 bp or 1090 bp, respectively, downstream from the beginning of the segment at the EcoRI site in the env gene. As shown in FIG. 1B, these sites are both upstream from the beginning of v-src. Treatment of the site with the Klenow fragment of E. coli DNA polymerase I creates a flush end, thereby preparing the site for subsequent ligation to the desired linker. Prior to attaching the linker, the deletion can be enlarged by digestion of the segment with an exonuclease such as Bal31 which sequentially removes individual base pairs from the cleaved end of the segment.

The downstream fragment endpoint can be created by digesting the 3.1 kb subclone with PvuII restriction enzyme thereby cleaving the DNA segment at a site 273 bp upstream from the downstream LTR. As in the creation of the upstream endpoint, the deletion can be enlarged with Bal31 or some other suitable exonuclease. Hereafter, all deleted variants are referred to by a first number identifying the upstream fragment endpoint followed by a second number identifying the downstream fragment endpoint of the v-src deletion. The upstream fragment endpoint is numbered from a conserved EcoRI site in env, and the downstream fragment endpoint is numbered relative to the beginning of the LTR or alternatively from the EcoRI site. A negative number designates a position upstream from the LTR. Viral DNA clone 1090/-29, for example, refers to a v-src deletion that has lost the region from the BalI site 1,090 base pairs downstream from the EcoRI site in env to a Bal131-created site 29 bp upstream from the downstream LTR. This same clone could also be designated 1090/2897. Because these vectors lack the oncogene of the original RSV, they are commonly referred to as ALV vectors.

For a replication competent vector, it is important not to delete any significant portion of the PPT which provides a cis-acting function necessary for retrovirus replication [Sorge et al., J. Virol. 43: 482–488 (Aug. 1982)]. In RSV, the PPT occurs at the 3' end of the direct repeat downstream from v-src, and just upstream from the $U_3$ region of the LTR as depicted in FIG. 1B. The PPT sequence, as well as the sequences representing the major portion of the direct repeat and the beginning of the $U_3$ are as follows:

```
ATCGAT(-69)
    ↓
GGGCTTCGGT TGTACGCGGT TAGGAGTCCC CTCAGGATAT
-70        -60        -50        -40
```

Sorge et al., supra, suggests that up to 29 nucleotide sequences including and flanking the PPT may be necessary for replication competency. For example, in the sequence depicted above when the downstream deletion endpoint is at −29, the virus is replication competent; whereas if the deletion endpoint is −8, the virus does not replicate. The ATCGAT's shown above the indicated endpoints represent alternate sites for inserted ClaI recognition sequences (linkers).

For efficient expression of the inserted gene, sequences that direct the transcription process must be preserved. As shown in FIG. 1B, RSV has a splice donor at the beginning of the gag gene and two splice acceptors. The first splice acceptor is near the end of pol just upstream from env. The natural splicing out of gag and pol allows for the expression of env. The second splice acceptor is upstream of src and is necessary for expression of the oncogene. By preserving that splice acceptor, the inserted segment can be expressed. As reported in Hughes and Kosik (Virol. 136: 89–99 (1984)], herein incorporated by reference, it is possible to insert the splice acceptor in inverted orientation and still retain functionality. An option to retaining the original splice acceptor is to insert one which has been produced synthetically. Alternatively, the inserted segment can include an internal promotor which would direct transcription of the foreign gene.

Parental RSV is susceptible to rearrangements that occur during viral replication. These rearrangements result in part from recombination events between noncoding regions flanking src which form a direct repeat 110 bases long in the SR-A strain. Such recombination events are extremely frequent and give rise to deleted viruses that lack the src region. Likewise, vector derivatives that contain the direct repeats rapidly lose sequences introduced in place of src during viral passage.

In order to stabilize the vector against elimination of the substituted gene, elimination of the homology between the noncoding regions is desirable. This can be accomplished by creating a series of defined deletions within the region between 743–1123 which lies between env and src or within the region 2073–2915 which lies between src and the PPT as shown in FIG. 1B. The 743–1123 region is relatively large (379 bases) and provides no functions essential for growth. In regard to the expression of src or a gene inserted in its place, it provides only a functional splice acceptor which can either be replaced or eliminated in favor of a promotor as previously discussed. If the upstream direct repeat in this region is deleted, then the downstream direct repeat must be preserved, and vice versa. Of course, as mentioned above, in deleting the downstream direct repeat the PPT must remain intact. No major role in replication has been ascribed to the E.T. segment, and therefore it is dispensible. The details of deleting extraneous segments in the construct are set forth in Hughes and Kosik (Virology 136: 89–99 (1984)], supra.

Although ClaI is not the only known restriction site which does not naturally occur in RSV DNA, it is a convenient choice for a synthetic site in the vector for src replacement. Several other sites could be chosen without materially affecting the invention. In constructing vectors having ClaI insertion sites, the ClaI linkers should be ligated to the endpoints of the upstream and downstream fragments. After digesting the subclones containing these fragments with ClaI, the fragments are then ligated together. The resultant vector has a ClaI site at the point of ligation. If the gene of interest is naturally flanked by ClaI or TaqI sites, it can be inserted into the vector after digestion of the gene and the vector with the enzyme. If ClaI sites are not present on either side of the gene, they can be added by ligating ClaI linkers in the same manner described in relation to the vector fragments. It is of course understood that other restriction sites could be introduced into the vector and endpoints of the gene of interest provided that they can be manipulated without altering any other essential functionality of the vector.

To facilitate the cloning into the viral vectors of a wide variety of different sequences, it is possible to use what we have termed an "adaptor" to convert virtually any DNA segment into a fragment with the ends necessary for insertion into the vector.

Figure 2:
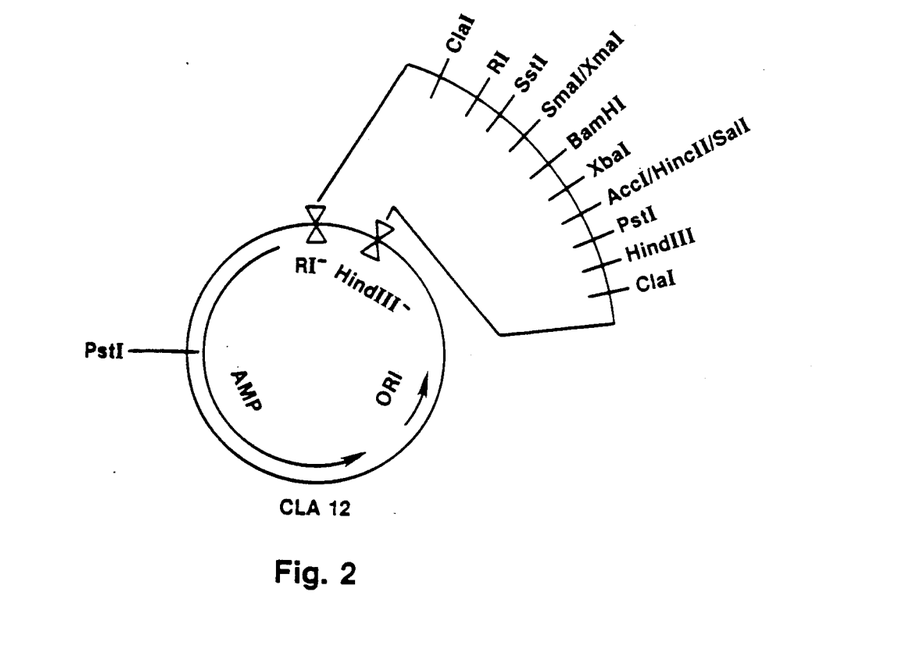
FIG. 2 is a schematic diagram of an adaptor for use in conjunction with gene insertion.

As illustrated in FIG. 2, the adaptors are miniplasmids having multiple cloning sites. In the simplest form, a ClaI adaptor comprises a pair of ClaI sites flanking a polylinker array; that is, an array of other restriction sites. The polylinker array is in a sequence chosen not to interfere with transcription or translation. These adaptors can be used to convert complete coding regions, containing a functional ATG and an appropriate leader sequence, to fragments having ClaI endpoints. These fragments can then be recovered by ClaI digestion and inserted into the vector.

In an alternate embodiment, the adaptor can supply an authentic eucaryotic 5' untranslated region and an appropriate initiation ATG. This allows the expression in the vector of segments that either lack a functional ATG or a functional leader or both. The adaptors can also supply a functional splice acceptor and can be used with a variety of promoters as well.

Constructs having the src gene replaced by a gene of interest and stabilized by elimination of the direct repeat homology are nonetheless characterized by a degree of oncogenicity which may well be considered objectionable in commercial poultry lines if they retain the original LTRs. We have discovered a solution to this problem. Almost all domestic chicken stocks have endogenous viral DNA in their germ lines. Although most of the endogenous proviruses are defective, a few are replication-competent. The ev2 endogenous locus in the chicken genome produces the replication-competent, Rous-associated virus (RAV-0), that has little or no oncogenic potential in vivo and has considerable homology with the ALV viruses. Substitutions of defined segments of RSV with corresponding segments of RAV-0 produce constructions designed to retain the useful features of the RSV vectors but with greatly reduced oncogenicity. Retaining the subgroup A env gene of the parental RSV vectors is particularly useful, since many domestic chickens have the subgroup A receptor. By contrast most domestic stocks lack the subgroup E receptor characteristic of RAV-0, and, as a consequence, cannot be readily infected by viruses carrying the endogenous subgroup env gene. Of course other envelope subgroups such as B, C, D, and F could be incorporated into the construction.

We and others have accumulated sufficient evidence that at least a portion of the oncogenic potential resides in the LTRs at the end of the viral genome. The LTRs contain the promoters and polyadenylation signals necessary for appropriate expression of the viral RNAs. Furthermore, the LTRs recombine with the host genome when viral DNA integrates therein to form the provirus. The RAV-0 LTR is significantly shorter than the LTR of RSV, being 278 (instead of 330) base pairs in length. The major differences between the RAV-0 LTR and the other replication-competent ASV-ALV LTRs (including RSV LTRs) lie in the $U_3$ segment of the LTR. The sequence of the RAV-0 LTR and adjoining regions is given in Hughes [J. Virol. 43(1): 191–200 (July 1982)], herein incorporated by reference. The ALV LTR contains a powerful enhancer that the RAV-0 LTR lacks. Accordingly, the RAV-0 virus replicates somewhat less efficiently than the corresponding ALVs. It seems likely that the lack of oncogenicity is also related to the absence of the powerful enhancer in the RAV-0 LTR.

Figure 3:
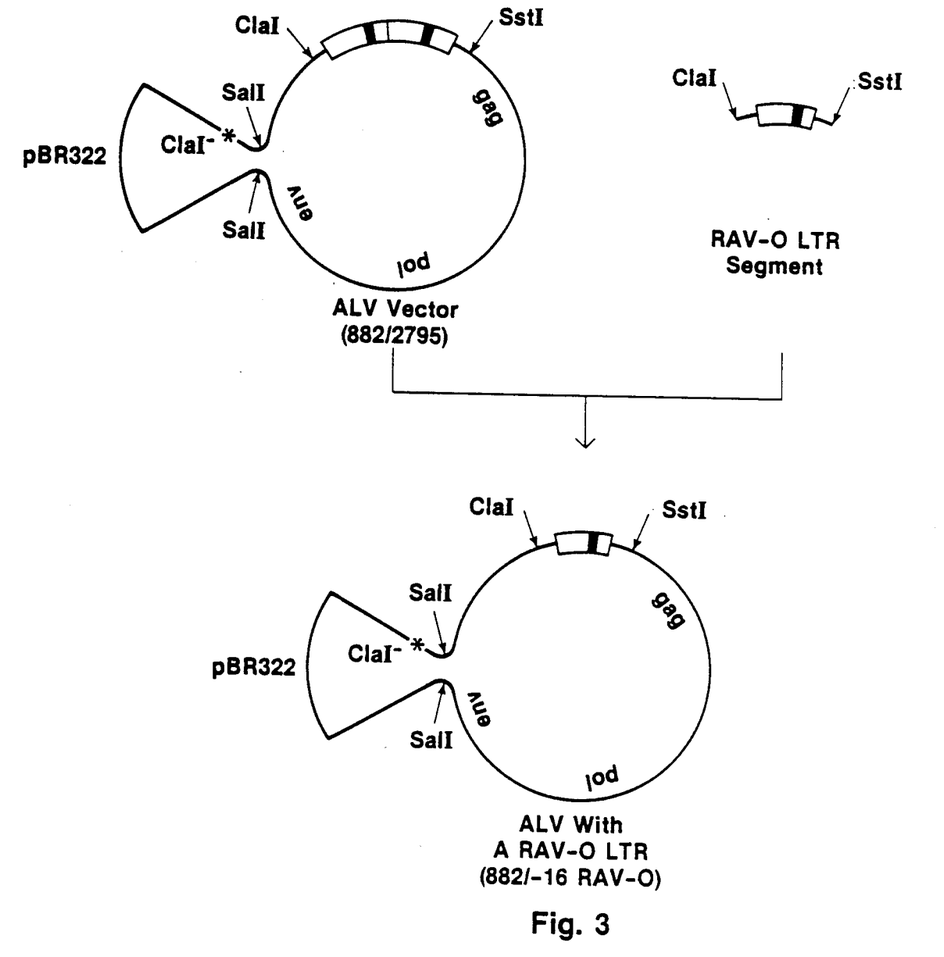
FIG. 3 is a schematic diagram illustrating the substitution of a RAV-0 LTR for the LTR of an RSV-derived vector in a pBR322-derived plasmid.

In the src replacement procedure described above, a synthetic ClaI site was introduced just between env and the LTR. A naturally occurring SstI site exists between the LTR and gag. Thus, it is a relatively straightforward process to excise the ALV LTR with the appropriate restriction enzymes. The RAV-0 clone has a corresponding SstI site between the LTR and gag. A synthetic ClaI site corresponding to that in the ALV construction can be introduced into the RAV-0 clone as follows. After digestion with the HindIII and Bal 31 exonuclease, synthetic ClaI linkers are inserted between env and the LTR of RAV-0. The precise location of the inserted linkers can be determined by DNA sequencing and the RAV-0 clones with ClaI sites that correspond to ClaI sites in the ALV vectors are selected. The ClaI to SstI piece containing the RAV-0 LTR is then substituted for the ClaI to SstI segment containing the ALV LTR as illustrated in FIG. 3. To facilitate the constructions, the substitutions are preferably done with a circularly permuted form of the viral DNA in a suitable plasmid. In FIG. 3, the plasmid segment is pPH, a derivative of pBR322 that lacks the ClaI site. We refer to this derivative as pPH. The plasmid was cloned into the SalI site that lies in the env gene of the viral vector. On the upper right of the figure is the ClaI to Sst fragment derived from a clone of the small circular form of RAV-0 DNA, which has only one LTR. At the bottom of the figure is shown the final recombinant with the RAV-0 LTR in the ALV virus.

The convention for naming the recombinant vectors is based on the distances of the site where the ClaI linker is inserted from defined landmarks in the parent virus. As with the src deletions, the first number designates a position downstream from the conserved EcoRI site. The second number refers to a position relative to the beginning of the RAV-0 LTR. Virus can be rescued from such construction by cutting with SalI to excise the plasmid sequences and ligating to concatermerize the permuted viral DNA. It is preferred that the ALV segment and the RAV-0 segment do not overlap to avoid creating a direct repeat flanking the ClaI site. Segments upstream from the RAV-0 LTR such as the PPT and the direct repeat region may be carried over with the LTR provided that the corresponding regions in the ALV fragment are deleted.

Vectors prepared in accordance with the aforementioned description are capable of expressing a variety of inserts under the direct control of the RAV-0 LTR. The level of expression is significantly lower than with the corresponding ALV constructions, probably reflecting the lack of a strong enhancer in the RAV-0 LTR.

Since the retroviral LTR is not normally a tissue specific promoter, it is recognized that constructions expressing genes under the control of the retroviral LTR may not show defined tissue specific expression when embedded in the germ line. Should tissue specific expression be a problem, there are possible alternatives to vector construction. One approach is to insert a foreign promoter linked directly to the gene of interest as previously discussed (Hughes et al., unpublished). Under this approach, the presence of the RAV-0 LTR is particularly fortuitous in that it lacks a strong enhancer and as a consequence is not as likely to interfere with the specificity of a foreign promoter.

Another possibility for achieving tissue specific expression would be to introduce enhancers into the RAV-0 LTR constructions so as to place the RAV-0 LTR promoter under the control of a foreign enhancer. With this approach, caution should be exercised in selecting an enhancer which does not subvert the reduced oncogenicity of the RAV-0 LTR.

As a preferred embodiment for commercial application, a one-round vector can also be constructed. This type of construction inserts the gene of interest into the genome of the first cell infected but is unable to replicate further. The host will thereby not carry a somatically replicating retrovirus with possible detrimental effects. The one-round feature can be incorporated into the aforementioned constructions in a variety of ways. One proposed system would operate as follows. The vector DNA would be made up of two LTRs, a segment recognized for RNA packaging, a promotor, and the gene of interest. The vector DNA would be inserted into a helper cell that contains and expresses all the viral genes but which cannot package into virions RNA segments from which these viral proteins derive. In contrast, the vector DNA would be transcribed to RNA that has appropriate packaging sequences and the other genes of interest, and this RNA is included in the progeny virion with all the viral proteins needed for infectivity and reverse transcription. When such a vector infects a cell, the vector DNA can be inserted in the host genome, but no progeny virus can be produced.

As a final step in producing the viral vector, the DNA construction produced in accordance with the above procedures must be transfected into cultured avian cells. If a permuted viral DNA is used, prior to transfection it must be separated from plasmid DNA by digestion with an appropriate restriction endonuclease and ligated to produce a complete provirus. Alternatively, a nonpermuted proviral form of the vector can be used without digestion or ligation.

Infection with the Retroviral Vector. Potential approaches for infecting avian embryos with retroviruses have been described by Crittenden et al. [Avian Dis. 30(1): 43–46 (1986)]and Crittenden et al. [Can. J. Anim. Sci. 65: 553–562 (Sept. 1985)]. In any of these approaches, either the nonpermuted proviral DNA or the viral form retroviral vector may be used. One such approach involves injecting the vector into multiple developing ova before ovulation [Shuman et al., Poult. Sci. 65: 1436–1444 (1986)]. This procedure exposes ova to the vector at the very early stages of development. The second approach involves binding the vector to sperm with an agent such as DEAE dextran or polybrene. Upon conventional artificial insemination of the female, the vector would presumably be carried by the sperm into the ovum. In accord with the third approach, the vector is injected in or near the germinal disc of newly laid fertile eggs. At this stage the embryo is made up of thousands of cells, but germinal primordia are still susceptible to infection. We have in fact now discovered that at least the latter approach to germ line insertion is feasible when applied to the vectors of this invention. Successful insertion is evidenced by stable inheritance after conventional breeding. That is, the gene of interest is inherited and expressed in a Mendelian fashion.

Practical applications of germ line insertion in accordance with this invention include: (1) transfer of beneficial genes from other species; (2) introduction of single beneficial genes into highly productive lines; (3) introduction of artificial genes; (4) amplification of beneficial gene expression; (5) inactivation of "undesirable" genes; (6) creation of chromosomal markers; and (7) identification of host genes which have major effects on economic traits.

As an illustration of the utility of the vectors of the invention, they could be used to insert genes for resistance to a specific disease or pathogen. For example, the introduction of the viral gene coding for the envelope antigen of subgroup A avian leukosis virus (ALV), if appropriately expressed and then localized in the cell membrane, should interfere with infection by the most common subgroup of ALV in chicken flocks. The endogenous viral gene ev6 represents a naturally occurring model for such a host gene. Ev6 encodes subgroup E envelope, but not for complete virus. Cells from chickens expressing ev6 are relatively resistant to infection with exogenous subgroup E viruses. Such a model suggests that chickens expressing subgroup A envelope should be relatively resistant to subgroup A ALVs. Other models currently being developed in mammalian systems for the expression of antigens and antibodies may also find application in the avian system. As previously mentioned, the inserted segments can range in size up to about 2 kb if the virus is replication competent. Defective viral vectors should be able to accept 7–8 kb of new sequences.

While the vectors disclosed herein have been principally designed for insertion of genetic material into an avian germ line, it is to be understood that they also find application for introduction of foreign genes into somatic cells both in vivo and in vitro. In this regard, the vectors would be useful for inserting and expressing genetic information into cells or tissue in individual birds or for production of proteins or other biological materials in cell culture.

The following examples are intended only to further illustrate the invention and are not intended to limit the scope of the invention which is defined by the claims.

EXAMPLE 1

Preparation of 882/-16 RAV-0. The starting material for constructing the vector was the large circular form of DNA from the SR-A strain of RSV, cloned as a permuted linear into λgtWES. Manipulations were performed on fragments subcloned into the plasmid pBR322 or a derivative of pBR322, pPH. The plasmids were grown in E. coli HB101, DH-1, or DH-5, amplified with chloramphenicol, and purified by RNase and pronase digestions of Triton X-100 lysates. Plasmid DNA to be 5' end labeled or digested with Bal31 exonuclease was passed over a "Bio-Gel" A-15M column to remove RNA or banded 2X in $CsCl_2$ ethidium bromide gradients.

Before the ALV LTR was replaced with the RAV-0 LTR, the v-src coding region was removed from subclones of SR-A DNA, creating a site for insertion of foreign DNA.

A λgtWES clone containing a permuted form of the large circular DNA from the SR-A strain of Rous sarcoma virus was obtained from W. DeLorbe [DeLorbe et al., J. Virol. 36: 50–61 (1980)]. The 3.1-kb EcoRI fragment containing the src gene (FIG. 1B) was subcloned into pBR322. A clone was chosen with the EcoRI site in env near the amp gene in pBR322. DNA from this plasmid was digested with AccI which cleaves the viral sequences at a position 882 bases from the EcoRI site in env (originally thought to be 884 bases from the EcoRI site) [Sorge et al., J. Mol. Appl. Genet. 1: 547–559 (1982)]. The AccI digested DNA was treated with the Klenow fragment of E. coli DNA polymerase I and then ligated with T4 DNA ligase in the presence of ClaI linkers. This DNA was used to transform E. coli HB101 and clones containing the ClaI linker were identified by ClaI digestion. The precise location of the ClaI linker was defined by DNA sequencing [Maxam et al., Meth. Enzymol. 65: 449–560 (1980)]. This segment was reassembled into several circularly permuted viral vectors that contained ALV LTRs [Maxam et al., Meth. Enzymol., (1980), supra]. For the 882/2795 construction that was used as a parent for the 882/-16 RAV-0 vector, a second ClaI linker was introduced 2795 bases from the EcoRI site in env. A second pBR322 subclone containing the 3.1-kb src EcoRI fragment in the orientation such that the EcoRI site in gag was adjacent to the amp gene in pBR322 was identified and the plasmid DNA digested with NruI. The digested DNA was treated with the Klenow fragment of E. coli DNA polymerase and ligated with T4 DNA ligase in the presence of ClaI linkers. This DNA was used to transform DH-1. Plasmids that had acquired a ClaI linker were identified by ClaI digestion. The site of insertion of the ClaI linker was verified by DNA sequencing. The 882 and 2795 segments were combined to recreate the circularly permuted 882/2795 vector [Hughes et al., Virology 136: 89–99 (1984), supra].

To permit the substitution of the RAV-0 LTR for the ALV LTR, the 882/2795 (ALV LTR) was digested with ClaI and SstI to remove the LTR-containing segment. There is a corresponding SstI site in the RAV-0 clone [Hughes, J. Virol. 43: (1982), supra], so that site did not require modification in the RAV-0 DNA. However, no ClaI site existed upstream of the RAV-0 LTR. To create the ClaI site near the RAV-0 LTR, the small circular form of unintegrated RAV-0 viral DNA containing one copy of the LTR was cloned as a partial EcoRI digest in Charon 3A, and the HindIII to EcoRI fragment containing the LTR was subcloned into pBR322. The DNA subclone was opened at the HindIII site in the env gene and treated with the double strand exonuclease Bal31 for varying periods of time (between 1 and 10 minutes). Aliquots from the Bal31 digests were analyzed by gel electrophoresis to measure the approximate number of base pairs removed. Since we wished to remove approximately 700 base pairs of viral information, time points were chosen in which 1200–1500 base pairs had been removed from the two ends of the DNA. DNA from appropriate time points was treated with the Klenow fragment of E. coli DNA polymerase I and ligated with T4 DNA ligase in the presence of synthetic ClaI linkers [Hughes, J. Virol. 43: (1982), supra]. This DNA was introduced into E. coli DH-1 and plasmids from individual clones were tested for the presence of a ClaI linker by digestion with ClaI. Plasmids that had lost approximately 700 bases of viral DNA and had acquired a ClaI site were chosen following ClaI/EcoRI double digestion. Appropriate clones were analyzed by DNA sequencing using the technique of Maxam et al. [Meth. Enzymol. 65: (1980), supra]. This defined precisely the position where the ClaI linker was inserted.

The stability of the sequences inserted into retroviral vectors depends on whether or not there are direct repeats flanking the insert [Sorge et al., Eukaryotic Viral Vectors (1982); Sorge et al., J. Mol. Appl. Genet. 1: 547–559 (1982), supra; Sorge et al., J. Virol. 48: 667–675 (1983); Hughes et al., Virology 136: (1984), supra]. Since the portion of the RAV-0 genome just upstream of the LTR has considerable homology to the region of the ALV genome just downstream of env [Hughes, J. Virol. 43: (1982), supra], it was important to obtain a ClaI linker at a position in the RAV-0 DNA that was matched to the site where the ClaI linker was inserted in 882/2795 (ALV LTR). In addition, the RAV-0 LTR segment must retain the polypurine tract required in cis for replication of the virus. An approximate RAV-0 LTR clone (called -16) that had the ClaI linker inserted 16 bases from the boundary between $U_3$ and the PPT was therefore selected.

The ClaI to SstI segment was isolated from the -16 clone and inserted between the ClaI and SstI sites of 882/2795 (ALV LTR) replacing the ALV LTR's (see FIG. 3). This vector has no direct repeats flanking the ClaI sites used for insertion of foreign DNA, and retains the splice acceptor necessary for expressing foreign sequences. The base sequence for 882/-16 RAV-0 between env and the LTR is shown below:

Cloned viral DNA was isolated from an *E. coli* culture after amplification with chloramphenicol, and banded twice in CsCl$_2$-ethidium bromide gradients. The DNA was extracted several times with isopropanol, once with a 1:1 phenol chloroform mixture, diluted tenfold and ethanol precipitated.

Before transfection, permuted viral DNA was released from plasmid DNA by digestion with the restriction endonuclease SalI, the site into which the permuted viral DNA had been cloned, and ligated with T4 DNA ligase at DNA concentration of 500 μg./ml. The ligation products were purified by phenol extraction and precipitated with ethanol. It is not necessary to remove the plasmid DNA before ligation. The concatemeric viral DNA was then introduced into susceptible chicken cells in culture by CaPO$_4$ mediated transfection. Virions are produced by the transfected cells and subsequently spread to all of the cells in culture by infection. High titer viral stocks are derived from the supernatants of such cultures.

Oncogenicity of the virus was determined by injection into fertilized eggs and newly hatched chicks. There is a small residual oncogenicitiy that does not interfere with the production of transgenic birds.

The 882/-16 RAV-0 vector as a derivative of pBR322 has been cloned in *E. coli* DH-1, and as such has been deposited under the Budapest Treaty with the Agricultural Research Service Culture Collection in Peoria, Ill., and has been assigned NRRL Accession No. B-18180.

EXAMPLE 2

Figure 4:
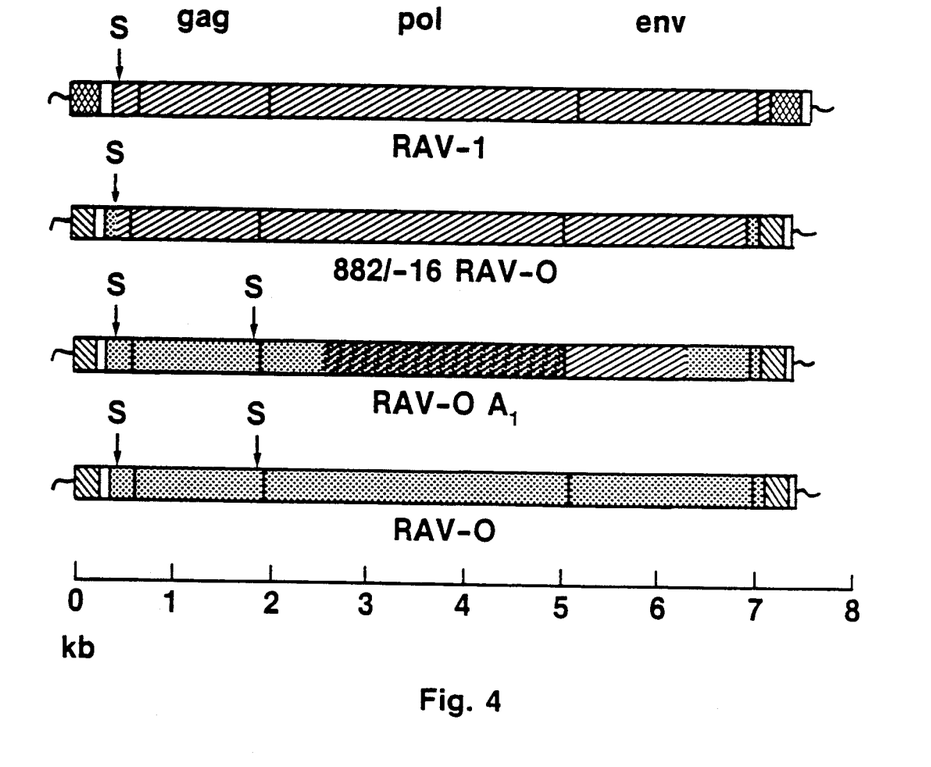
FIG. 4 is a sequence of schematic diagrams illustrating the various retroviruses and vectors employed in the experiment set forth in Example 2.

The effectiveness of germ line insertion by the recombinant 882/-16 RAV-0 constructed in Example 1 as compared to nonvector ALV viruses was demonstrated as follows: exogenous and recombinant ALV were injected into the yolk near the developing embryo of Line 0 eggs, a line of chickens lacking endogenous viral genes [Astrin et al., Nature 282: 339-341 (1979)], just before incubation. Three subgroup A ALVs were used. The molecular map of each natural and recombinant virus as it appears in proviral form integrated in host DNA is shown in FIG. 4. For reference, the molecular map of RAV-0 is also shown. As in FIG. 1, the coding regions for each proviral form are: gag, group-specific antigens; pol, polymerase; and env, envelope. The LTRs are represented at the ends of the integrated proviral genomes by enclosed and open boxes. RAV-1 is a highly pathogenic exogenous virus. RAV-0-A$_1$ is less pathogenic than RAV-1. It is a recombinant strain containing mostly RAV-0 viral information, including its LTR, and the subgroup A envelope determinant and, perhaps, most of the polymerase gene of Schmidt-Ruppin A [Wright and Bennett, Virus Research (in press)]. Note that the LTR from RAV-1 is approximately 100 bases longer than the LTR from RAV-0, and both recombinant viruses, RAV-0-A$_1$ and 882/-16 RAV-0, contain the RAV-0 LTR and variable amounts of the coding regions of RAV-0 and RAV-1 as illustrated. RAV-0 like coding sequences are indicated by the dotted area and RAV-1-like sequences by the hatched area. Also note that most of the polymerase gene in RAV-0-A$_1$ could be either like RAV-0 or RAV-1. S with arrow indicates SacI restriction enzyme sites in proviral genome. Host DNA is indicated by wavy line. Since exogenously infected males have been shown not to transmit congenitally whereas exogenously infected females do [Rubin et al., Proc. Natl. Acad. Sci. USA 47: 1058-1069 (1961); Spencer et al., Cold Spring Harbor Conference on Cell Proliferation 7: 553-564 (1980)], we assumed that if infection of germ cells had occurred then the viremic males would transmit proviral information at a measurable frequency to the next generation with little confusion from congenital transmission.

The procedure for infection was as follows: the eggs were placed in egg cartons large end up so that the yolk would reorient and the blastoderm would lie approximately underneath the air cell. The surface of the egg was wiped with a sterile gauze soaked in 10% Roccal II solution and then wiped with an ethanol-soaked sterile gauze. A small hole was drilled into the shell at the large end of the egg by hand and shell dust was removed with an ethanol-soaked sterile gauze. Virus (50 μl.) was injected into the yolk with a repeating 3-ml. syringe and ½-in. 26- or 30-gauge needle. The surface of the egg was wiped again with an ethanol-soaked sterile gauze and the hole sealed with "Duco" fast-drying glue. Trial injections of dye showed that some of the material was injected into the upper yolk area just underneath or beside the blastoderm. Eggs were then incubated in a standard egg incubator. After hatching, each chick was identified by wingband, vaccinated against Marek's disease with HVT/SB-1 bivalent vaccine [Witter et al., Avian Pathol. 13: 75-92 (1984)], and a small quantity of blood was removed from a leg vein with a lancet and a heparanized capillary tube for dot-blot analysis. Chicks positive for ALV proviral DNA were housed in modified Horsfall-Bauer stainless steel isolators for 4 to 6 weeks with oxytetracycline hydrochloride antibiotic ("Pura-mycin," Ralston Purine Company; diluted according to manufacturer's recommendations) for the first 2 weeks. Those chicks infected with RAV-1 were treated with milbolerone in the drinking water at a concentration of 0.5 g./ml. for 4 weeks to prevent retrovirus-induced bursal lymphomas [Kakuk et al., Avian Dis. 21: 280-289 (1977)]. Each surviving viremic male, which is designated generation (G0), was mated to at least two specific-pathogen-free line 0 females. The progeny from each mating, designated generation 1

(G1), were assayed for integrated proviral DNA sequences by a DNA dot-blot procedure with an ALV probe. This was possible because we used Line 0 chickens which had no background of endogenous proviral genes when assayed with stringent hybridization and washing techniques. Dot-blot positive G1 progeny were easily visualized. One of 14, 4 of 14, and 4 of 9 RAV-1, RAV-0-A$_1$, and 882/-16 RAV-0 viremic males, respectively, transmitted viral information to their G1 progeny at frequencies varying from 1 to 11%. Twenty-three of the 28 dot-blot positive progeny have been preliminarily characterized by restriction enzyme analysis. DNA from the blood of dot-blot positive G1 progeny was digested with Sac I restriction enzyme and transferred to a solid support (see FIG. 1 for restriction sites in the viruses) and probed with an ALV probe. This tests whether the provirus resides in the same place in the DNA of the parent and the offspring. If the transmitted viral information had been acquired congenitally in somatic cells only, then the restricted DNA would appear as a smear of proviral junction fragments representing viral integration at many different sites. In contrast, genetically acquired proviral genomes should have only one or several proviral junction fragments. All of the 23 dot-blot positive G1 progeny had different simple restriction enzyme fragments of from one to three junction fragments. In addition, 22 of the 23 positive G1 progeny were also positive for infectious ALV with titers from $10^5$ to $10^7$ infectious units per milliliter of whole blood.

The G1 dot-blot positive progeny were raised to maturity, mated to specific-pathogen-free Line 0 males and females and their progeny (G2) screened for active viral genetic material in blood samples by ELISA for viral antigens [Smith et al., Avian Dis. 23: 698–707 (1979)], for integrated viral genomes by the DNA dot-blot procedure described above and for comparison with their parents of the sites of integration of the proviruses. Table I summarizes the transmission data from three of the G0 viremic males (all three viruses are represented) to their G1 male and female progeny and subsequent transmission from some of the dot-blot positive G1 progeny to their G2 progeny. As stated previously, these three G0 viremic males are mosaic, since the viral information was transmitted at low frequencies to their G1 progeny (2%, 5%, and 0.8% for RAV-1, RAV-0-A$_1$, and 882/-16 RAV-0, respectively). The positive G1 progeny from each viremic G0 male had simple proviral junction fragments, whereas the viremic male parent had many proviral junctions which appeared as a smear in the autoradiogram.

Male G1 progeny wingband number V-19282 from G0 RAV-1 viremic male showed junction fragments of 20 and 8.4 kb. The G2 progeny of male V-19282 were analyzed as described above. As shown in Table I, 13 of 33 progeny (39%) were positive for proviral genomes and viral synthesis by both dot-blot and ELISA procedures. Each positive G2 progeny inherited both 20 and 8.4 kb junction fragments from its male parent.

Female G1 progeny wingband number U-22066 of 882/-16 RAV-0 viremic G0 male showed a single junction fragment of 8.5 kb As shown in Table I, 43 of 44 of the G2 progeny (98%) were positive for proviral genomes and viral antigens by dot-blot and ELISA techniques. A proportion of G2 progeny from G1 female parents having an active proviral genome may become infected congenitally. Some of the positive progeny inherited the single proviral genome and the remainder of the positive progeny had proviral junction fragments appearing as a smear on the autoradiograph. Those progeny containing many fragments represent congenital (non-genetic) transmission.

Female G1 progeny wingband number U-26358 of RAV-0-A$_1$ viremic G0 male showed major junction fragments of 10.8 and 7.5 kb and a minor internal fragment of 1.5 kb. The presence of the minor internal fragment is predicted from the molecular map of RAV-0-A$_1$ in FIG. 5. As shown in Table I, 43 of 52 of the G2 progeny (83%) were positive for proviral sequences and viral antigens by dot-blot and ELISA techniques. In those birds with germline insertions, the major junction fragment segregated appropriately demonstrating germline insertion.

Progeny test data on a total of 23 G1 inserts confirmed that avian retroviruses can be inserted into the chicken germ line by the relatively simple technique of injecting fertile eggs with live retroviruses. Of 921 G2 progeny tested, 439 (48%) contained the G1 parental junction fragment. This close fit to the 50% transmission of the insert expected, based on Mendelian inheritance, clearly shows germline insertion and stable inheritance.

The fact that one of the viruses successfully inserted (882/-16 RAV-0 of Example 1) is a vector, opens the way for the insertion of foreign genes into the avian germ line for conducting basic studies of gene expression in the avian system, and eventually to introduce genes that may be used for poultry improvement.

TABLE I

Transmission of ALV Proviral DNA from the G0 Viremic Male Parents to the G1 Progeny and From the G1 Progeny to Their G2 Progeny

| Virus | G0 Viremic 0 wingband number | G1 Number dot-blot positive/ total | G1 Wingband number (sex) | G2 Number dot-blot positive/ total |
|---|---|---|---|---|
| RAV-1 | U-20113 | 2/98 | V-19282 (♂) | 13/33 |
| RAV-0-A(1) | U-19772 | 7/134 | U-26358 (♀) | 43/52 |
| 882/-16 RAV-0 | U-19637 | 1/119 | U-22066 (♀) | 43/44 |

Total all 23 inserts: 439 out of 921 (47.7%)

It is understood that the foregoing detailed description is given merely by way of illustration and that modification and variations may be made therein without departing from the spirit and scope of the invention.

We claim:

1. A method for inserting a foreign gene into an avian genome comprising transfecting an avian cell with the vector 882/-16 RAV-0 incorporating said foreign gene, wherein said transfection is promoted by injection of said vector into the blastoderm of an egg of said avian.

2. A method as described in claim 1 wherein said foreign gene is inserted into the avian genome and is capable of producing infectious virus within said cell.

3. A method for inserting a foreign gene into an avian genome comprising transfecting an avian germinal cell with the vector 882/-16 RAV-0 incorporating said foreign gene and promoting the embryonic development of said cell.

4. A method as described in claim 3 wherein said foreign gene is inserted into the avian genome and is capable of producing infectious virus within said cell.

* * * * *